(12) United States Patent
Welz-Biermann et al.

(10) Patent No.: US 7,202,379 B2
(45) Date of Patent: Apr. 10, 2007

(54) PROCESS FOR THE PREPARATION OF BIS(PERFLUOROALKYL)PHOSPHINIC ACIDS AND SALTS THEREOF

(75) Inventors: Urs Welz-Biermann, Heppenheim (DE); Nikolai Ignatyev, Duisburg (DE); Michael Weiden, Darmstadt (DE); Udo Heider, Winchester (GB); Andri Kucheryna, Duisburg (DE); Helge Willner, Muehlheim/Ruhr (DE); Peter Sartori, Utting (DE)

(73) Assignee: Merck Patent GmbH, Darmstadt (DE)

( * ) Notice: Subject to any disclaimer, the term of this patent is extended or adjusted under 35 U.S.C. 154(b) by 183 days.

(21) Appl. No.: 10/511,157

(22) PCT Filed: Mar. 17, 2003

(86) PCT No.: PCT/EP03/02740

§ 371 (c)(1),
(2), (4) Date: Oct. 14, 2004

(87) PCT Pub. No.: WO03/087110

PCT Pub. Date: Oct. 23, 2003

(65) Prior Publication Data

US 2005/0256334 A1 Nov. 17, 2005

(30) Foreign Application Priority Data

Apr. 16, 2002 (DE) .................... 102 16 997

(51) Int. Cl.
*C07F 9/22* (2006.01)
(52) U.S. Cl. ............................ 562/8; 562/26
(58) Field of Classification Search ............... None
See application file for complete search history.

(56) References Cited

FOREIGN PATENT DOCUMENTS

SU           498311        1/1976
WO    WO 30 002579        1/2003

OTHER PUBLICATIONS

Kovaleva et al. Perfluoroalkylphosphonic Acids and Their Derivatives. Journal of General Chemistry USSR, Bd. 59, Nr. 3, 1989, p. 2245-2248.*
Yagupol' Skii L M; "Electrochemical Fluorination of Trialkylphosphine Oxides" Journal of General Chemistry of the USSR, Consultants Bureau, New York, NY, US Bd. 54, Nr. 4, Part. 1, Apr. 1984, pp. 692-695.
Chemical Abstracts, vol. 84, No. 15, Apr. 12, 1976, Columbus, Ohio, US, abstract No. 105768, Semenii, V. Ya et al.: "Bis (Perfluoroalkyl) Phosphinic Acids".
Mahmood, Tariq et al.: "Comparative Study of Tris (Trifluoromethyl) Phosphine Oxide, Tris (Nonafluorobutyl) Phosphine Oxide and Fluorobis (Nonafluorobutyl) Phosphine Oxide with Ammonia and Amines" Inorganic Chemistry (1988), 27(17, 2913-16.
Pavlenko N.V. et al.: "Esters of Bis(Perfluoroalkyl) Phosphinic Acids" Journal of General Chemistry USSR., Bd 59, Nr. 3, Aug. 20, 1989, pp. 474-476.

* cited by examiner

*Primary Examiner*—Sikarl A. Witherspoon
(74) *Attorney, Agent, or Firm*—Millen, White, Zelano, Branigan, P.C.

(57) ABSTRACT

The present invention relates to a process for the preparation of bis(perfluoroalkyl)phosphinic acids comprising at least the reaction of at least one difluorotris(perfluoroalkyl)phosphorane or at least one trifluorobis(perfluoroalkyl)phosphorane with hydrogen fluoride in a suitable reaction medium, and heating of the resultant reaction mixture. The invention also relates to salts of bis(perfluoroalkyl)phosphinic acids and to the use thereof.

18 Claims, No Drawings

PROCESS FOR THE PREPARATION OF BIS(PERFLUOROALKYL)PHOSPHINIC ACIDS AND SALTS THEREOF

This application claims priority to PCT/EP03/02740 filed 17 Mar. 2003 and DE 10216997 filed 16 Apr. 2002.

The present invention relates to a process for the preparation of bis(perfluoroalkyl)phosphinic acids comprising at least the reaction of at least one difluorotris(perfluoroalkyl) phosphorane or at least one trifluorobis(perfluoroalkyl) phosphorane with hydrogen fluoride in a suitable reaction medium, and heating of the resultant reaction mixture. The invention also relates to salts of bis(perfluoroalkyl)phosphinic acids and to uses thereof.

Bis(perfluoroalkyl)phosphinic acids have been known for some time and are suitable for the preparation of various chemicals, such as, for example, corresponding methyl esters, which are strong methylating reagents (N. V. Pavienko et al., Zh. Obshch. Khim., 59, No. 3 (1989), pages 534–537). Bis(perfluoroalkyl)phosphinic acids and their corresponding salts are furthermore used on the basis of their surface-active action (DE-A 22 33 941; N. N. Kalibabchuk et al., Teor. Eksp. Khim., 11, No. 6 (1975), pages 838–841; N. N. Kalibabchuk et al., Ukr. Khim. Zh., 44, No. 1 (1978), pages 67–70) and in fuel cells (T. Mahmood, Inorganic Chemistry, 25 (1986), pages 3128–3131).

The lithium salt of bis(pentafluoroethyl)phosphinic acid is a highly promising candidate for use as conductive salt in lithium batteries (F. Kita et al., Proc. Electrochem. Soc., 99-25, (2000), pages 480–484; F. Kita et al., J. Power Sources, 90, No. 1 (2000), pages 27–32).

Bis(trifluoromethyl)phosphinic acid is prepared by hydrolysis of bis(trifluoromethyl)phosphorus trichloride, which is accessible with difficulty (H. J. Emeleus et al., J. Chem. Soc. (1955), pages 563–574). The higher homologues of bis(trifluoromethyl)phosphinic acid have been obtained from the corresponding difluorotris(perfluoroalkyl)phosphoranes (V. Ya. Semenii et al., U.S.S.R. Patent 498, 311).

The literature discloses essentially two different processes for the preparation of bis(perfluoroalkyl)phosphinic acids.

In the first process, a difluorotris(perfluoroalkyl)phosphorane is, in a first step, reacted with hexamethyldisiloxane to give the corresponding phosphine oxide. This is then followed in a second step by hydrolysis to the corresponding bis(perfluoroalkyl)phosphinic acid. This process has the disadvantage that the temperature during the hydrolysis must be controlled and regulated very precisely and only extremely small amounts of the desired bis(perfluoroalkyl) phosphinic acid are usually obtained (T. Mahmood, Inorganic Chemistry, 25 (1986), pages 3128–3131; U.S.S.R. Patent, 498,311; pages 57–61; T. Mahmood et al., Inorganic Chemistry, 27 (1988), pages 2913–2916).

A further known process is the direct hydrolysis of difluorotris(perfluoroalkyl)phosphoranes to bis(perfluoroalkyl)phosphinic acids (T. Mahmood et al, Inorganic Chemistry, 27 (1988), pages 2913–2916). It is disadvantageous in this process that, owing to the very poor miscibility of the phosphoranes with water, in particular of the phosphoranes with long alkyl chains, the hydrolysis proceeds only very slowly and usually results in very complex product mixtures.

The object of the present invention was therefore to provide a process which enables the simple and inexpensive preparation of bis(perfluoroalkyl)phosphinic acids in good yields. The bis(perfluoroalkyl)phosphinic acids should preferably be obtained in high purity. A further object was to provide salts of bis(perfluoroalkyl)phosphinic acids.

This object has been achieved by the process according to the invention for the preparation of bis(perfluoroalkyl)phosphinic acids which comprises at least the following process steps:
a) reaction of at least one difluorotris(perfluoroalkyl) phosphorane or at least one trifluorobis(perfluoroalkyl) phosphorane with hydrogen fluoride in a suitable reaction medium, and
b) heating of the reaction mixture obtained in a).

Difluorotris(perfluoroalkyl)phosphoranes and trifluorobis (perfluoroalkyl)phosphoranes can be prepared by conventional methods known to the person skilled in the art.

These compounds are preferably prepared by electrochemical fluorination of suitable starting compounds, as described in V. Ya. Semenii et al., Zh. Obshch. Khim., 55, No. 12 (1985), pages 2716–2720; N. lgnatiev, J. of Fluorine Chem., 103 (2000), pages 57–61 and WO 00/21969. The corresponding descriptions are hereby incorporated by way of reference and are regarded as part of the disclosure.

It is also possible to employ mixtures of two or more difluorotris(perfluoroalkyl)phosphoranes and/or two or more trifluorobis(perfluoroalkyl)phosphoranes in the process according to the invention. Preferably, in each case only one difluorotris(perfluoroalkyl)phosphorane or trifluorobis (perfluoroalkyl)phosphorane is employed in the process according to the invention.

In a preferred embodiment of the process according to the invention, use is made of at least one difluorotris(perfluoroalkyl)phosphorane or at least one trifluorobis(perfluoroalkyl)phosphorane of the general formula I

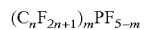

where $1 \leq n \leq 8$, preferably $1 \leq n \leq 4$, and m in each case=2 or 3.

Particularly preferred difluorotris(perfluoroalkyl)phosphorane compounds can be selected from the group consisting of difluorotris(pentafluoroethyl)phosphorane, difluorotris(n-nonafluorobutyl)phosphorane and difluorotris(n-heptafluoropropyl)phosphorane.

A particularly preferred trifluorobis(perfluoroalkyl)phosphorane compound which can be employed in the process according to the invention is trifluorobis(n-nonafluorobutyl) phosphorane.

The reaction of at least one difluorotris(perfluoroalkyl) phosphorane or at least one trifluorobis(perfluoroalkyl) phosphorane with hydrogen fluoride in a suitable reaction medium is preferably carried out in a process as described in DE 101 30 940.6. The corresponding description is hereby incorporated by way of reference and is regarded as part of the disclosure.

The temperature for the heating of the reaction mixture obtained in process step a) in process step b) is preferably from room temperature to 150° C., particularly preferably from 100° C. to 145° C. and very particularly preferably from 135 to 140° C.

The reaction mixture obtained in process step a) is preferably heated in process step b) for from 1 to 150 hours, particularly preferably for from 10 to 25 hours and very particularly preferably for from 18 to 22 hours.

If desired, it may be advantageous again to add some of the same or another reaction medium to the reaction mixture during the heating in process step b).

In order to accelerate the hydrolysis, the reaction mixture obtained in process step a) can preferably also be heated in a closed, pressure-tight apparatus, such as, for example, an autoclave, at elevated temperature, preferably of from 140° C. to 200° C.

Besides the desired bis(perfluoroalkyl)phosphinic acids, the reaction in accordance with the process according to the invention gives hydrogen fluoride and in each case the corresponding monohydroperfluoroalkane as further reaction products.

These reaction products can, if desired, be separated off, if desired collected and if desired isolated by conventional methods which are familiar to the person skilled in the art, for example by condensation in suitable cold traps.

Hydrogen fluoride and monohydroperfluoroalkanes are themselves valuable chemical raw materials which can be utilised usefully. Thus, it is possible, inter alia, to collect and recycle the hydrogen fluoride so that it is available for the reaction in process step a).

If necessary, the preparation of bis(perfluoroalkyl)phosphinic acids by the process according to the invention can be followed by purification and, if desired, isolation of these compounds by conventional methods which are familiar to the person skilled in the art.

The purification is preferably carried out by distillation, preferably under reduced pressure at elevated temperatures.

The respective salts of bis(perfluoroalkyl)phosphinic acid can preferably be isolated by neutralisation of bis(perfluoroalkyl)phosphinic acids.

The salts are prepared from the respective bis(perfluoroalkyl)phosphinic acid by reaction with at least one conventional base which is known to the person skilled in the art, preferably in solution.

In order to prepare the salts, bis(perfluoroalkyl)phosphinic acids are neutralised using bases, preferably selected from the group consisting of the hydroxides, oxides, hydrides, amides, carbonates, phosphines and amines.

After the neutralisation, the salt formed is worked up in a manner known to the person skilled in the art. The salt can be washed and subsequently dried.

The application also relates to salts of bis(perfluoroalkyl) phosphinic acids selected from the group consisting of partially alkylated and peralkylated ammonium, phosphonium, sulfonium, pyridinium, pyridazinium, pyrimidinium, pyrazinium, imidazolium, pyrazolium, thiazolium, oxazolium and triazolium salts salts. Preference is given to the preparation of salts of bis(perfluoroalkyl)phosphinic acids having a cation selected from the group consisting of

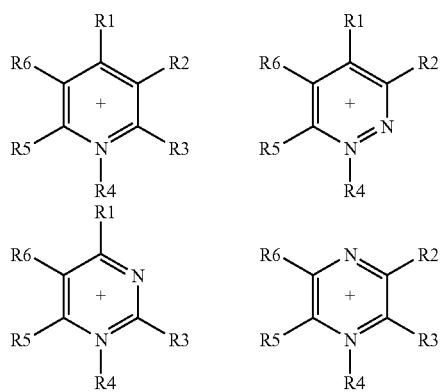

-continued

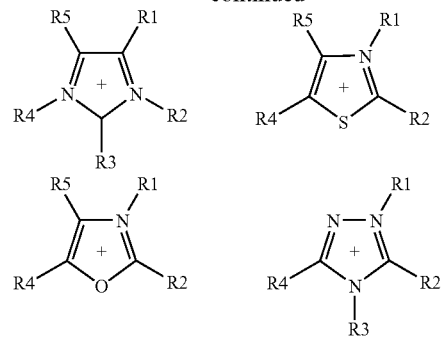

where $R^1$ to $R^5$ are identical or different, are optionally bonded directly to one another by a single or double bond and are each, individually or together, defined as follows:
H,
halogen, where the halogens are not bonded directly to N,
an alkyl radical ($C_1$ to $C_8$), which may be partially or completely substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$, $C_nF_{(2n+1-x)}H_x$, where $1<n<6$ and $0<x\leq 2n+1$.

Surprisingly, it has been found that these salts can be used as ionic liquids, phase-transfer catalysts or surfactants.

The process according to the invention for the preparation of bis(perfluoroalkyl)phosphinic acids enables the simple, inexpensive and reliable preparation of these compounds in very good yields. Bis(perfluoroalkyl)phosphinic acids are usually obtained in high purity without further complex purification steps. Through the reaction with bases, salts can be obtained which were hitherto not available It is furthermore advantageous that the by-products obtained in the process according to the invention, namely hydrogen fluoride and monohydroperfluoroalkanes, are themselves valuable raw materials which can be utilised usefully. This enables the environmental impact in the reaction in accordance with the process according to the invention to be kept low and the costs for the process according to the invention to be reduced.

The invention is explained below with reference to examples. These examples serve merely to explain the invention and do not restrict the general inventive idea.

EXAMPLES

The NMR spectra were recorded using a Bruker Avance 300 NMR spectrometer at the following frequencies:
300.1 MHz $^1$H
282.4 MHz for $^{19}$F and
121.5 MHz for $^{31}$P.

Example 1

Synthesis of bis(pentafluoroethyl)phosphinic acid $(C_2F_5)_2P(O)OH$ a)
3.53 g of water (corresponding to a total amount of water in the mixture of 294 mmol) were added to 2.93 g of 40% by weight hydrofluoric acid (corresponding to 58.6 mmol of HF) in an FEP (fluoroethylene polymer) flask. The resultant mixture was then cooled using an ice bath. 25.03 g (58.7 mmol) of difluorotris(pentafluoroethyl)phosphorane, $(C_2F_5)_3PF_2$, were subsequently added over the course of 3 minutes with stirring using a magnetic stirrer. The difluorotris(pentafluoroethyl)phosphorane dissolved completely within a further three minutes, and a colourless, clear solution of $H^+[(C_2F_5)_3PF_3]^-$ in water was obtained.

The resultant solution was stirred at room temperature for a further 15 minutes and subsequently refluxed at an oil-bath temperature of from 135 to 140° C. for 14 hours. A further 4.83 g of water were subsequently added to the solution, and the mixture was refluxed at the same temperature for a further 6 hours. After cooling to room temperature, 24.81 g of a clear solution were obtained.

3.95 g of a two-phase liquid were collected in an intermediate trap cooled with dry ice. This liquid comprised 2.11 g of $C_2F_5H$, 1.5 g of HF and 0.34 g of the starting compound difluorotris(pentafluoroethyl)phosphorane.

In order to isolate bis(pentafluoroethyl)phosphinic acid, aqueous. hydrogen fluoride solution was distilled off from the reaction mixture, giving 15.13 g of virtually pure bis (pentafluoroethyl)phosphinic acid. The yield was 86.5%, based on the difluorotris(pentafluoroethyl)phosphorane employed.

For further purification, the bis(pentafluoroethyl)phosphinic acid was distilled under reduced pressure at 125 Pa. The boiling point was 63–64° C.

The resultant bis(pentafluoroethyl)phosphinic acid was characterised by means of $^{19}F-$, $^{31}P-$ and $^1H$-NMR spectroscopy and by elemental analysis:

$^{19}F$-NMR spectrum; δ, ppm:
(solvent acetone-$D_6$, reference $CCl_3F$)
−80.55 s ($CF_3$); −125.37 d ($CF_2$); $J^2_{P,F}$=78.2 Hz
$^1H$-NMR spectrum; δ, ppm:
(solvent acetone-$D_6$, reference TMS)
12.71 br. s (OH)
$^{31}P$-NMR spectrum; δ, ppm:
(solvent acetone-$D_6$, reference 85% by weight $H_3PO_4$)
−0.03 quin; $J^2_{P,F}$=78.3 Hz The values of the chemical shifts found correspond to the values disclosed in the publication by T. Mahmood, Inorganic Chemistry, 25 (1986), pages 3128–3131.

Elemental analysis:
Found: C, 15.76%; H, 0.40%.
Calculated for (($C_2F_5)_2P(O)OH$): C, 15.91%; H, 0.33%.

b)
2.50 g of water (corresponding to a total amount of water in the mixture of 166.5 mmol) were added to 0.834 g of a 40% by weight aqueous hydroflouric acid (corresponding to 16.7 mmol of HF) in an FEP flask. The resultant mixture was then cooled using an ice bath. 7.11 g (16.7 mmol) of difluorotris(pentafluoroethyl)phosphorane, $(C_2F_5)_3PF_2$, were finally added over the course of three minutes with stirring using a magnetic stirrer. The difluorotris(pentafluoroethyl)phosphorane dissolved completely within a further three minutes, and a colourless, clear solution of $H^+[(C_2F_5)_3PF_3]^-$ in water was obtained. The reaction mixture was refluxed at an oil-bath temperature of 115° C.–120° C. for 108 hours. In order to isolate the bis(pentafluoroethyl) phosphinic acid, water/HF solution were distilled off from the reaction mixture, giving 3.97 g of virtually pure bis (pentafluoroethyl)phosphinic acid, $(C_2F_5)_2P(O)OH$. The yield was 78.8%, based on the difluorotris(pentafluoroethyl) phosphorane employed. The resultant product was characterised by means of $^{19}F$-NMR spectroscopy. The corresponding signals corresponded to the signals mentioned under Example 1a.

c)
2.59 g (56.2 mmol) of ethanol were cooled in an FEP vessel using an ice bath. Firstly 0.49 g (24.5 mmol) of hydrogen fluoride (HF) was slowly added to the ethanol with stirring using a magnetic stirrer, and 9.59 g (22.5 mmol) of difluorotris(pentafluoroethyl)phosphorane, $(C_2F_5)_3PF_2$, were added to the reaction mixture over the course of a further three minutes. After the phosphorane had dissolved, 2.21 g (122.6 mmol) of water were added to the solution, and the reaction mixture were refluxed at an oil-bath temperature of 120° C. for 144 hours (2.1 g of water were added to the reaction mixture after. 44 hours and a further 2.0 g of water were added after 94 hours).

In order to isolate the bis(pentafluoroethyl)phosphinic acid, ethanol/water/HF solution were distilled off from the reaction mixture, giving 5.21 g of virtually pure bis(pentafluoroethyl)phosphinic acid, $(C_2F_5)_2P(O)OH$. The yield was 76.6%, based on the difluorotris(pentafluoroethyl)phosphorane employed. The resultant product was characterised by means of $^{19}F$-NMR spectroscopy. The corresponding signals corresponded to the signals indicated under Example 1a.

Example 2

Synthesis of bis(n-nonafluorobutyl)phosphinic acid
(n-$C_4F_9)_2P(O)OH$ a)
4.25 g of water (corresponding to a total amount of water in the mixture of 371 mmol) were added to 4.07 g of a 40% by weight hydrofluoric acid (corresponding to 81.4 mmol of HF) in an FEP (fluoroethylene polymer) flask. The resultant mixture was then cooled using an ice bath. 51.42 g (70.8 mmol) of difluorotris(n-nonafluorobutyl)phosphorane, (n-$C_4F_9)_3PF_2$, were subsequently added over the course of 10 minutes with stirring using a magnetic stirrer.

The resultant solution was stirred at room temperature for a further 20 minutes and subsequently refluxed at an oil-bath temperature of from 135 to 140° C. for 11.5 hours. A further 5.00 g of water were subsequently added to the solution, and the mixture was refluxed at the same temperature for a further 8.5 hours. After cooling to room temperature, 46.47 g of a clear solution were obtained. 15.03 g of a two-phase liquid were collected in an intermediate trap cooled with dry ice. This liquid comprised 13.06 g of n-$C_4F_9H$ and 1.97 g of HF (upper phase).

In order to isolate the bis(n-nonafluorobutyl)phosphinic acid, aqueous hydrogen fluoride solution was distilled off from the reaction mixture at an oil-bath temperature of 145° C., giving 34.62 g of virtually pure bis(n-nonafluorobutyl) phosphinic acid as a solid. The yield was 97.4%, based on the difluorotris(n-nonafluorobutyl)phosphorane employed.

For further purification, the bis(n-nonafluorobutyl)phosphinic acid was distilled under reduced pressure at 125 Pa. The boiling point was 124° C. During cooling, the resultant bis(n-nonafluorobutyl)phosphinic acid solidifies to give a solid having a melting point of 103–104° C.

In the literature publication by T. Mahmood, Inorganic Chemistry, 25 (1986), pages 3128–3131, bis(n-nonafluorobutyl)phosphinic acid is described as a non-volatile liquid, which is probably a hydrated form of this compound.

Bis(n-nonafluorobutyl)phosphinic acid was characterised by means of $^{19}F-$, $^{31}P-$ and $^1H$-NMR spectroscopy and by elemental analysis:

$^{19}$F-NMR spectrum; δ, ppm:
(solvent acetone-D$_6$, reference CCl$_3$F)
−80.90 t (CF$_3$); −120.50 br. s (CF$_2$); −121.38 d (CF$_2$); −125.58 m (CF$_2$); J$^2$$_{P,F}$=79.5 Hz, J$^4$$_{F,F}$=9.9 Hz
$^1$H-NMR spectrum; δ, ppm:
(solvent acetone-D$_6$, reference TMS)
9.25 br. s (OH)
$^{31}$P-NMR spectrum; δ, ppm:
(solvent acetone-D$_6$, reference 85% by weight H$_3$PO$_4$)
1.74 quin; J$^2$$_{P,F}$=79.0 Hz
The values of the chemical shifts found correspond to the values disclosed in the publication by T. Mahmood, Inorganic Chemistry, 25 (1986), pages 3128–3131.
Elemental analysis: Found: C, 19.05%; H, 0.20%. Calculated for ((n-C$_4$F$_9$)$_2$P(O)OH): C, 19.14%; H, 0.20%.
b)
1.45 g of water (corresponding to a total amount of water in the mixture of 116.1 mmol) were added to 1.08 g of a 40% by weight aqueous hydroflouric acid (corresponding to 21.6 mmol of HF) in an FEP flask. The resultant mixture was then cooled using an ice bath. 7.98 g (15.2 mmol) of trifluorobis(n-nonafluorobutyl)phosphorane, (C$_4$F$_9$)$_2$PF$_3$, were finally added over the course of 10 minutes with stirring using a magnetic stirrer. The reaction mixture was stirred at room temperature for 15 hours and subsequently refluxed at an oil-bath temperature of 110° C. for 35 hours (a further 0.6 g of water was added to the reaction mixture after 17 hours and a further 1.2 g of water were added after 25 hours). In order to isolate the bis(n-nonafluorobutyl)phosphinic acid, water/HF solution were distilled off from the reaction mixture, giving 6.34 g of virtually pure bis(n-nonafluorobutyl)phosphinic acid. The yield was 83.2%, based on the trifluorobis(n-nonafluorobutyl)phosphorane employed. The resultant product was characterised by means of $^{19}$F-NMR spectroscopy. The corresponding signals corresponded to the signals mentioned under Example 2a.

Example 3

3.07 g of the bis(pentafluoroethyl)phosphinic acid prepared as described in Example 1 were neutralised in 50 cm$^3$ of water using 7.48 g of a 20% by weight aqueous solution of tetraethylammonium hydroxide. The water was subsequently evaporated off, and the resultant residue was dried under reduced pressure of 120 Pa at 70° C. (bath temperature).

4.38 g of white solid of tetraethylammonium bis(pentafluoroethyl)phosphinate having a melting point of 100–102° C. were obtained. The yield is virtually quantitative, based on the bis(pentafluoroethyl)phosphinic acid employed.

The tetraethylammonium bis(pentafluoroethyl)phosphinate was characterised by means of $^{19}$F—, $^{31}$P— and $^1$H-NMR spectroscopy and by elemental analysis:
$^{19}$F-NMR spectrum; δ ppm:
(solvent acetone-D$_6$, reference CCl$_3$F)
−80.23 s (CF$_3$); −124.90 d (CF$_2$); J$^2$$_{P,F}$=64.8 Hz
$^1$H-NMR spectrum; δ, ppm:
(solvent acetone-D$_6$, reference TMS)
1.36 tm (CH$_3$); 3.48 q (CH$_2$); J$^3$$_{H,H}$=7.3 Hz
$^{31}$P-NMR spectrum; δ, ppm:
(solvent acetone-D$_6$, reference 85% by weight H$_3$PO$_4$)
0.28 quin; J$^2$$_{P,F}$=64.5 Hz
Elemental analysis:
Found: C, 33.36%; H, 4.60%; N, 3.22%.
Calculated for (C$_2$F$_5$)$_2$P(O)ON(C$_2$H$_5$)$_4$: C, 33.42%; H, 4.67%; N, 3.25%.

Example 4

2.52 g of bis(pentafluoroethyl)phosphinic acid prepared as described in Example 1 were neutralised in 20 cm$^3$ of water using 0.577 g of potassium carbonate. The water was subsequently evaporated, and the resultant residue was dried under reduced pressure at 120 Pa and a bath temperature of 100° C. 2.83 g of white solid of potassium bis(pentafluoroethyl)phosphinate were obtained. The yield is virtually quantitative, based on the bis(pentafluoroethyl)phosphinic acid employed. The salt decomposed at a temperature of 203–205° C.

The potassium bis(pentafluoroethyl)phosphinate was characterised by means of $^{19}$F— and $^{31}$P-NMR spectroscopy and by elemental analysis:
$^{19}$F-NMR spectrum; δ, ppm:
(solvent acetone-D$_6$, reference CCl$_3$F)
−80.40 m (CF$_3$); −125.11 d (CF$_2$); J$^2$$_{P,F}$=67.4 Hz
$^{31}$P-NMR spectrum; δ, ppm:
(solvent acetone-D$_6$, reference 85% by weight H$_3$PO$_4$)
0.73 quin; J$^2$$_{P,F}$=67.2 Hz
Elemental analysis:
Found: C, 14.6%.
Calculated for (C$_2$F$_5$)$_2$P(O)OK: C, 14.13%.

Example 5

4.00 g of bis(n-nonafluorobutyl)phosphinic acid prepared as described in Example 2 were neutralised in 50 cm$^3$ of water using 5.86 g of a 20% by weight aqueous solution of tetraethylammonium hydroxide. In the process, a white precipitate formed, which was filtered off and dried under reduced pressure of 120 Pa and at a bath temperature of 70° C. 4.93 g of white solid of tetraethylammonium bis(n-nonafluorobutyl)phosphinate having a melting point of 99–100° C. were obtained. The yield was 98%, based on the bis(n-nonafluoroethyl)phosphinic acid employed.

The tetraethylammonium bis(n-nonafluorobutyl)phosphinate was characterised by means of $^{19}$F—, $^{31}$P— and $^1$H-NMR spectroscopy and by elemental analysis:
$^{19}$F-NMR spectrum; δ, ppm:
(solvent acetone-D$_6$, reference CCl$_3$F)
−80.75 tt (CF$_3$); −120.35 m (CF$_2$); −121.17 dm (CF$_2$); −125.30 m (CF$_2$); J$^2$$_{P,F}$=65.0 Hz; J$^4$$_{F,F}$=9.9 Hz, J$_{F,F}$=3.1 Hz
$^1$H-NMR spectrum; δ, ppm:
(solvent acetone-D$_6$, reference TMS)
1.37 tm (CH$_3$); 3.48 q (CH$_2$); J$^3$$_{H,H}$=7.3 Hz
$^{31}$P-NMR spectrum; δ, ppm:
(solvent acetone-D$_6$, reference 85% by weight H$_3$PO$_4$)
1.70 quin; J$^2$$_{P,F}$=64.9 Hz
Elemental analysis:
Found: C, 30.32%; H, 3.05%, N, 2.10.
Calculated for (n-C$_4$F$_9$)$_2$P(O)ON(C$_2$H$_5$)$_4$: C, 30.44%; H, 3.19%; N, 2.22.

Example 6

1.93 g (6.39 mmol) of bis(pentafluoroethyl)phosphinic acid prepared as described in Example 1 were neutralised in 50 cm$^3$ of water using a solution of 0.371 g (3.19 mmol) of 1,6-diaminohexane in 15 cm$^3$ of water. The water was evaporated off, and the resultant residue was dried under reduced pressure at 120 Pa and a bath temperature of 100° C. 2.21 g of white solid of hexamethylene-1,6-diammonium bis(pentafluoroethyl)phosphinate having a melting point of 208–210° C. were obtained. The yield was 96.1%, based on the bis(pentafluoroethyl)phosphinic acid employed.

The hexamethylene-1,6-diammonium bis(pentafluoroethyl)phosphinate was characterised by means of $^{19}$F—, $^{31}$P— and $^1$H-NMR spectroscopy and by elemental analysis:

$^{19}$F-NMR spectrum; δ, ppm:
(solvent DMSO-D$_6$, reference CCl$_3$F)
−79.59 m (CF$_3$); −124.66 ppm d (CF$_2$); $J^2_{P,F}$=65.6 Hz $^1$H-NMR spectrum; δ ppm:
(solvent DMSO-D$_6$, reference TMS)
1.30 m (2CH$_2$); 1.51 m (2CH$_2$); 2.76 m (2CH$_2$), 7.53 br. s (2NH$_3^+$)

$^{31}$P-NMR spectrum; δ, ppm:
(solvent DMSO-D$_6$, reference substance 85% by weight H$_3$PO$_4$)
−2.15 quin; $J^2_{P,F}$=65.5 Hz Elemental analysis:
Found: C, 23.61%; H, 2.49%; N, 4.07%.
Calculated for [(C$_2$F$_5$)$_2$P(O)O]$_2^{2-}$[H$_3$N(CH$_2$)$_6$NH$_3$]$^{2+}$ C 23.35%; H 2.52%; N 3.89%.

Example 7

2.80 g (5.58 mmol) of bis(n-nonafluorobutyl)phosphinic acid prepared as described in Example 2 were neutralised in 50 cm$^3$ of water using a solution of 0.324 g (2.79 mmol) of 1,6-diaminohexane in 15 cm$^3$ of water. In the process, a white precipitate formed, which was filtered off and dried under reduced pressure at 120 Pa and a bath temperature of 100° C. 2.87 g of white solid of hexamethylene-1,6-diammonium bis(n-nonafluorobutyl)phosphinate having a melting point of >250° C. were obtained. The yield was 92%, based on the bis(n-nonafluorobutyl)phosphinic acid employed.

The hexamethylene-1,6-diammonium bis(n-nonafluorobutyl)phosphinate was characterised by means of $^{19}$F—, $^{31}$P— and $^1$H-NMR spectroscopy and by elemental analysis:

$^{19}$F-NMR spectrum; δ, ppm:
(solvent DMSO-D$_6$, reference CCl$_3$F)
−80.03 t (CF$_3$); −120.46 m (CF$_2$); −121.28 dm (CF$_2$), −125.11 m (CF$_2$), $J^2_{P,F}$=65.6 Hz, $J^4_{F,F}$=9.5 Hz $^1$H-NMR spectrum; δ, ppm:
(solvent DMSO-D$_6$, reference TMS)
1.29 m (2CH$_2$); 1.51 m (2CH$_2$); 2.76 m (2CH$_2$), 7.61 br. s (2NH$_3^+$)

$^{31}$P-NMR spectrum; δ, ppm:
(solvent DMSO-D$_6$, reference 85% by weight H$_3$PO$_4$)
−0.76 quin; $J^2_{P,F}$=65.5 Hz Elemental analysis:
Found: C, 23.76%; H, 1.58%; N, 2.48%.
Calculated for: [(C$_4$F$_9$)$_2$P(O)O]$_2^{2-}$[H$_3$N(CH$_2$)$_6$NH$_3$]$^{2+}$ C 25.59; H 1.62%; N 2.50%.

Example 8

2.23 g (4.44 mmol) of bis(n-nonafluorobutyl)phosphinic acid prepared as described in Example 2 were neutralised in 50 cm$^3$ of water using a solution of 1.20 g (4.45 mmol) of tri-n-hexylamine in 20 cm$^3$ of a 1:1 (vol/vol) water/ethanol mixture. 15 cm$^3$ of ethanol were subsequently added, and the mixture was refluxed for 5 minutes.

After cooling to room temperature, a white precipitate formed, which was filtered off and dried under reduced pressure at 120 Pa and a bath temperature of 60° C. 3.22 g of white solid of tri-n-hexylammonium bis(n-nonafluorobutyl)phosphinate having a melting point of 74–75° C. were obtained. The yield was 93.9%, based on the bis(n-nonafluorobutyl)phosphinic acid employed.

The tri-n-hexylammonium bis(n-nonafluorobutyl)phosphinate was characterised by means of $^{19}$F—, $^{31}$P— and $^1$H-NMR spectroscopy and by elemental analysis:

$^{19}$F-NMR spectrum; δ, ppm:
(solvent acetone-D$_6$, reference CCl$_3$F)
−80.82 tt (CF$_3$); −120.36 m (CF$_2$); −121.32 dm (CF$_2$), −125.53 m (CF$_2$); $J^2_{P,F}$=70.1 Hz; $J^4_{F,F}$=9.9 Hz, $J_{F,F}$=3.0 Hz $^1$H-NMR spectrum; δ, ppm:
(solvent acetone-D$_6$, reference TMS)
0.89 m (3CH$_2$); 1.35 m (9CH$_2$); 1.82 m (3CH$_2$); 3.21 m (2CH$_2$); 9.62 br. s (NH$^+$)

$^{31}$P-NMR spectrum; δ, ppm:
(solvent acetone-D$_6$, reference 85% by weight H$_3$PO$_4$)
1.76 quin; $J^2_{P,F}$=70.1 Hz Elemental analysis:
Found: C, 40.51%; H, 5.20%; N, 1.80%.
Calculated for (C$_4$F$_9$)P(O)O$^-$ $^+$HN(C$_6$H$_{13}$)$_3$: C, 40.45%; H, 5.22%; N, 1.82%.

Example 9

1.55 g (3.09 mmol) of bis(n-nonafluorobutyl)phosphinic acid prepared as described in Example 2 in 15 cm$^3$ of water are mixed with a solution of 1.20 g (3.09 mmol) of triphenylbenzylphosphonium chloride in 30 cm$^3$ of water, and the mixture is stirred at room temperature for 5 minutes. In the process, a white precipitate formed, which is filtered off and dried under reduced pressure at 120 Pa and a bath temperature of 60° C. 2.50 g of white solid of triphenylbenzylphosphonium bis(n-nonafluorobutyl)phosphinate having a melting point of 138–139° C. are obtained. The yield is 95.1% on the bis(n-nonafluorobutyl)phosphinic acid employed.

Triphenylbenzylphosphonium bis(n-nonafluorobutyl)phosphinate is characterised by means of $^{19}$F—, $^{31}$P— and $^1$H-NMR spectroscopy and by elemental analysis:

$^{19}$F NMR spectrum, δ, ppm:
(solvent: acetone-D6; reference: CCl$_3$F):
−80.76 t (CF$_3$); −120.36 m (CF$_2$); −121.21 dm (CF$_2$); −125.38 m (CF$_2$); $J^2_{P,F}$=65.9 Hz, $J^4_{F,F}$=9.9 Hz.

$^1$H NMR spectrum, δ, ppm:
(solvent: acetone-D6; reference: TMS):
5.22 d (CH$_2$, PhCH$_2$); 7.11–7.17 m (2H, PhCH$_2$); 7.19–7.27 m (2H, PhCH$_2$)
7.30–7.37 m (iH, PhCH$_2$); 7.72–7.87 m (12H, 3Ph); 7.91–7.99 m (3H, 3Ph) $J^2_{P,H}$=15.1 Hz.

$^{31}$P NMR spectrum, δ, ppm:
(solvent: acetone-D6; reference: 85% by weight H$_3$PO$_4$):
1.78 quin; 25.68 br.s; $J^2_{P,F}$=65.8Hz.

Elemental analysis:
Found: C, 46.10%; H, 2.48%.
Calculated for [(C$_4$F$_9$)$_2$P(O)O]$^-$[(C$_6$H$_5$)$_3$C$_6$H$_5$CH$_2$P]$^+$: C, 46.39%; H, 2.60%.

Example 10

A solution of 2.08 g (11.9 mmol) of 1-butyl-3-methylimidazolium chlorides in 3 cm$^3$ of water is added at room temperature to 4.05 g (11.9 mmol) of the potassium bis(pentafluoroethyl)phosphinate prepared as described in Example 4 in 15 cm$^3$ of water with constant stirring. In the process, an oily precipitate formed. The water is evaporated off under reduced pressure, and the resultant residue is dried under reduced pressure of 120 Pa and a bath temperature of 60° C. for 1 hour. 10 cm$^3$ of isopropyl alcohol are subsequently added to the residue, and a white precipitate is filtered off and washed twice with 5 cm$^3$ of isopropyl alcohol. The isopropyl alcohol is evaporated off under reduced pressure, and the resultant residue is dried under reduced pressure of 120 Pa and a bath temperature of 80° C. for 2 hours.

4.99 g of an oily liquid of 1-butyl-3-methylimidazolium bis(pentafluoroethyl)phosphinate are obtained. The yield is 95.4%, based on the potassium bis(pentafluoroethyl)phosphinate employed.

1-Butyl-3-methylimidazolium bis(pentafluoroethyl)phosphinate was characterised by means of $^{19}F$, $^{31}P$ and $^1H$-NMR spectroscopy:

$^{19}F$ NMR spectrum, ppm:
(solvent: acetonitrile-$D_3$; reference: $CCl_3F$):
−80.19 m ($CF_3$); −124.93 d ($CF_2$); $J^2_{P,F}$=66.9 Hz.

$^1H$ NMR spectrum, ppm:
(solvent: acetonitrile-$D_3$; reference: TMS):
0.93 t (3H, $CH_3$); 1.33 tq (2H, $CH_2$); 1.83 tt (2H, $CH_2$); 3.87 s (3H, $CH_3$); 4.17 t (2H, $CH_2$); 7.48 dd (1H) 7.54 dd (1H); 8.99 s (1H); $J^3_{H,H}$=1.6 Hz; $J^3_{H,H}$=7.3 Hz; $J^3_{H,H}$=7.6 Hz.

$^{31}P$ NMR spectrum, ppm:
(solvent: acetonitrile-$D_3$; reference: 85% $H_3PO_4$):
−1.86 quin; $J^2_{P,F}$=66.8 Hz.

The invention claimed is:

1. A process for the preparation of a bis(perfluoroalkyl) phosphinic acid or salt comprising:
   a) reaction of at least one difluorotris(perfluoroalkyl) phosphorane or at least one trifluorobis(perfluoroalkyl) phosphorane with hydrogen fluoride in a reaction medium, and
   b) heating of the reaction mixture obtained in a).

2. A process for the preparation of a bis(perfluoroalkyl) phosphinic acid or salt according to claim 1, wherein the salts are prepared by subsequent neutralisation.

3. A process according to claim 1, wherein the difluorotris (perfluoroalkyl)phosphorane or trifluorobis(perfluoroalkyl) phosphorane employed is a compound of the general formula I $$(C_nF_{2n+1})_mPF_{5-m} \qquad I$$

in which $1 \leq n \leq 8$, preferably $1 \leq n \leq 4$, and m in each case=2 or 3.

4. A process according to claim 1, wherein the difluorotris (perfluoroalkyl)phosphorane is difluorotris(pentafluoroethyl)phosphorane, difluorotris(n-nonafluorobutyl)phosphorane or difluorotris(n-heptafluoropropyl)phosphorane.

5. A process according to claim 1, wherein the trifluorobis (perfluoroalkyl)phosphorane compound is trifluorobis(n-nonafluorobutyl)phosphorane.

6. A process according to claim 1, wherein the temperature during the heating in process step b) is from room temperature to 150° C.

7. A process according to claim 1, wherein the duration of the heating in process step b) is from 1 to 150 hours.

8. A process according to claim 1, wherein the reaction medium is water or a water-based mixture.

9. A process according to claim 2, wherein bases, are used to prepare the salts.

10. A salt of a bis(perfluoroalkyl)phosphinic acid that is partially alkylated or peralkylated phosphonium, sulfonium, pyridinium, pyridazinium, pyrimidinium, pyrazinium, imidazolium, pyrazolium, oxazolium or triazolium.

11. A bis(perfluoroalkyl)phosphinic acid according to claim 10, having a cation that is where $R^1$ to $R^5$ are identical or different, are optionally bonded directly to one another by a single or double bond and are each, individually or together, defined as follows:
H,
halogen, where the halogens are not bonded directly to N,
an alkyl radical ($C_1$ to $C_8$), which may be partially or completely substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$, $C_nF_{(2n+1-x)}H_x$, where $1<n<6$ and $0<x \leq 2n+1$.

12. An ionic liquid comprising a bis(perfluoroalkyl)phosphinic acid according to claim 10.

13. A phase-transfer catalyst or surfactant comprising a salt of a bis(perfluoroalkyl)phosphinic acid according to claim 10.

14. A process according to claim 9, wherein said bases is a hydroxide, oxide, hydride, amide, carbonate, phosphine or amine.

15. A process according to claim 7, wherein the duration of the heating in process step b) is from 10 to 25 hours.

16. A process according to claim 7, wherein the duration of the heating in process step b) is from 18 to 22 hours.

17. A process according to claim 6, wherein the temperature during the heating in process step b) is from 100° C. to 145° C.

18. A process according to claim 6, wherein the temperature during the heating in process step b) is from 135 to 140° C.

* * * * *

UNITED STATES PATENT AND TRADEMARK OFFICE
CERTIFICATE OF CORRECTION

PATENT NO. : 7,202,379 B2
APPLICATION NO. : 10/511157
DATED : April 10, 2007
INVENTOR(S) : Urs Welz-Biermann Page 1 of 1

It is certified that error appears in the above-identified patent and that said Letters Patent is hereby corrected as shown below:

On the title page, item [75] Inventors: line 5, reads "Andri" should read -- Andriy --
Column 11, line 33, reads "neutralisation." should read -- neutralization. --
Column 11, line 41, reads "case=2or 3" should read -- case = 2 or 3. --
Column 11, line 56, reads "wherein bases, are used" should read -- wherein bases are used --

Column 12, line 20, reads "  --

Column 12, line 49, reads "said bases is" should read -- said base is --

Signed and Sealed this

First Day of April, 2008

JON W. DUDAS
*Director of the United States Patent and Trademark Office*